United States Patent [19]

Miragaya

[11] Patent Number: 5,735,992
[45] Date of Patent: Apr. 7, 1998

[54] POLISHING DEVICE WITH SAMPLE HOLDER

[75] Inventor: Jose Miragaya, Pierrevert, France

[73] Assignee: Commissariat a L'Energie Atomique, Paris, France

[21] Appl. No.: 628,636

[22] PCT Filed: Aug. 16, 1995

[86] PCT No.: PCT/FR95/01085

§ 371 Date: Sep. 19, 1996

§ 102(e) Date: Sep. 19, 1996

[87] PCT Pub. No.: WO96/05497

PCT Pub. Date: Feb. 22, 1996

[30] Foreign Application Priority Data

Aug. 17, 1994 [FR] France ................................ 94 10079

[51] Int. Cl.⁶ ................................................ B44C 1/22
[52] U.S. Cl. .................................. 156/345; 216/88
[58] Field of Search ................ 156/345 LP; 438/690, 438/691, 692; 216/38, 88, 89, 90, 91

[56] References Cited

U.S. PATENT DOCUMENTS

| | | | |
|---|---|---|---|
| 3,549,439 | 12/1970 | Kaveggia et al. | 156/345 X |
| 4,534,536 | 8/1985 | Nelson et al. | 249/83 |
| 4,600,469 | 7/1986 | Fusco et al. | 156/345 X |
| 5,593,537 | 1/1997 | Cote et al. | 156/345 X |

FOREIGN PATENT DOCUMENTS 90 10 700   9/1990   Germany.

*Primary Examiner*—William Powell
*Attorney, Agent, or Firm*—Oblon, Spivak, McClelland, Maier & Neustadt, P.C.

[57] ABSTRACT

The invention relates to a sample or specimen polishing device having a sample or specimen holder (15), which can be placed in an orifice of the support disk and holds the sample or specimen to be polished without the latter having previously been encapsulated with resin.

6 Claims, 2 Drawing Sheets

POLISHING DEVICE WITH SAMPLE HOLDER

TECHNICAL FIELD

The present invention relates to a device for polishing samples of materials provided with a sample holder. It is more particularly used in metallography.

PRIOR ART

In metallography, analyses of samples or specimens of materials generally require a thorough preparation of the sample which it is wished to analyze. The process generally used for preparing the sample to be analyzed consists of:

encapsulating the material sample in a resin in order to allow easier handling of the sample, demoulding the encapsulated sample, cutting up the encapsulated sample by means of a diamond cutter, so as to obtain a substantially planar sample surface, polishing said substantially planar surface on an abrasive paper in order to improve its planeity and then polishing said same planar surface on a cloth in contact with a diamond-containing liquid in order to finish the polishing of the sample.

In order to implement the polishing operations of the preparation process of the sample to be analyzed, use is generally made of a polishing device like those proposed by BUEHLER. Several types of polishing device are described in the commercial documentation distributed by BUEHLER.

These commercially available polishing devices comprise a polishing plate or table, a polishing head having a sample support disk, as well as a polishing head control system. In such devices, the resin-encapsulated and cut up samples are in each case placed in an orifice of the support disk. It is obvious that each of these samples is placed in said orifice in such a way that its cut surface is directed towards the polishing table.

On said polishing table can be place different types of abrasive papers (e.g. 180, 400, 80 or even 1200 μm) or a cloth to which has been added a diamond-containing liquid. Thus, the cut surface of each sample is rubbed on the polishing table with a view to finishing the planeity of said surface.

Such a process suffers from the disadvantage of requiring the encapsulation with resin of the sample to be analyzed. This sample encapsulation is essentially needed in order to maintain the sample in the support disk orifice during sample polishing.

Macrographic and micrographic observations can then be made of the polished sample. However, for sample analysis, i.e. the developing of the micro-structure of said material sample, it is necessary to carry out either a chemical etching, or a thermal etching. In most cases, no matter whether a chemical or a thermal etching is involved, it is necessary to strip the sample, because the generally used encapsulating resin is unable to withstand high temperatures (in the case of a thermal etching) or excessively corrosive media (in the case of a chemical etching). In addition, the most widely used procedure for stripping the sample of its resin involves slight heating so as to expand the resin and only recover the material sample. Only then can a chemical or thermal etching be carried out to reveal or develop the micro-structure of said material.

Moreover, in the case where it is wished to collect the sample, with a view to recovering the material in the case of radioactive materials (e.g. plutonium) or carry out a chemical or thermal etching as explained hereinbefore, it is necessary to use special resins which can be removed by slight heating. However, the resins used for encapsulating radioactive material samples are generally contaminated and must consequently be decontaminated or stored, which leads to supplementary waste or treatments.

Another disadvantage of this sample encapsulating process is its performance cost, because it involves encapsulating the sample with resin, then solidifying the resin, cutting up the encapsulated resin and finally polishing the encapsulated resin, which involves a relatively long time and therefore a high cost.

DESCRIPTION OF THE INVENTION

The object of the invention is to obviate the aforementioned disadvantages. To this end, it proposes a material sample polishing device in which the samples can be placed without having to be previously encapsulated in resin. The device has a sample holder which can be fitted into an orifice of any random, commercially available support disk.

More specifically, the invention relates to a device for polishing samples of materials, each having a substantially planar face. This polishing device has a polishing table, as well as a polishing head equipped with a support disk provided with at least one orifice. This device is characterized in that it also has a sample holder, which can at least partly be housed in the orifice of the disk, so as to be able to maintain the sample to be polished in a chosen position. This sample holder incorporates:

a central body having a lower portion incorporating means for holding and positioning the sample, and an upper portion having a base, in which are inserted means for regulating the depth reading of the sample in the orifice of the disk, a sliding jacket placed around the central body and having externally a shoulder, which subdivides said jacket into a stop ring having an external perimeter approximately equal to that of the base of the central body, and a smaller perimeter centring ring adjusted to the perimeter of the disk orifice.

According to the invention, the means for regulating the depth reading of the sample have three screws arranged regularly with respect to one another (e.g. at 120° from one another) and whose heads bear on the rear face of the stop ring of the sliding jacket.

According to a feature of the invention, the sample holding and positioning means comprise a planar support on which is positioned the sample, a fixed jaw integral with the central body and a mobile jaw positioned parallel to the fixed jaw and which together form a vice able to maintain the sample in the chosen position and at least one tightening screw in order to move the mobile jaw with respect to the fixed jaw.

According to a feature of the invention, the sample support has a V-shaped, transverse notch in which the sample is deposited, its planar face being oriented in a direction opposite to that of the notch.

According to another feature of the invention, one of the jaws of the sample holding and positioning means has a V-shaped axial notch in which the sample is locked, its planar face to be polished being oriented in a direction perpendicular to that of the notch.

According to an embodiment of the invention, the sample holder can have a cover, which can be fitted around the lower portion of the central body, so as to position the planar face of the sample parallel to the support.

DETAILED DESCRIPTION OF EMBODIMENTS

Figure 1:
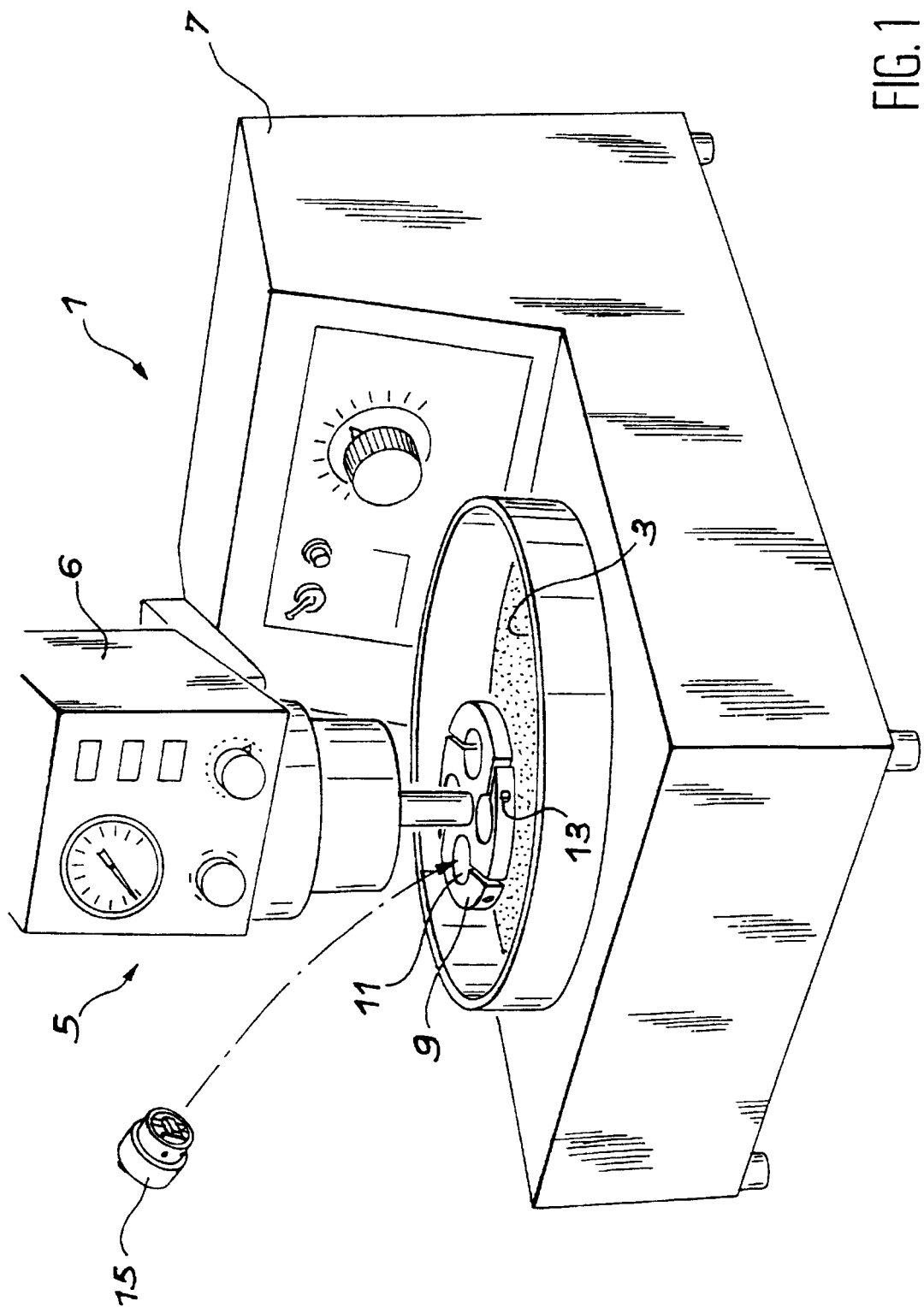
FIG. 1 shows a polishing device according to the invention and in which can be inserted a sample holder.

FIG. 1 shows the polishing device according to the invention. This polishing device 1 has, as in the prior art, a polishing table 3 in which can be deposited different types of abrasive paper or a cloth to which has been added a diamond-containing liquid, so as to permit a polishing of varying fineness of the material sample to be studied.

This polishing device 1 also has a polishing head 5 at least partly controlled by the control station 7. The polishing head 5 has a checking and measuring system 6 and a support disk 9. The support disk 9 is provided with one or more orifices 11. Four of these orifices 11 are shown in FIG. 1.

According to the invention, the sample holder 15 is introduced into one of the orifices 11 of the support disk 9. More specifically, the sample holder 15 is positioned in the orifice 11 by means of a shoulder, which will be described in greater detail in conjunction with FIG. 2. When the sample holder 15 has been correctly positioned in the orifice 11, a screw system 13 maintains the sample holder 15 in the chosen position.

Figure 2:
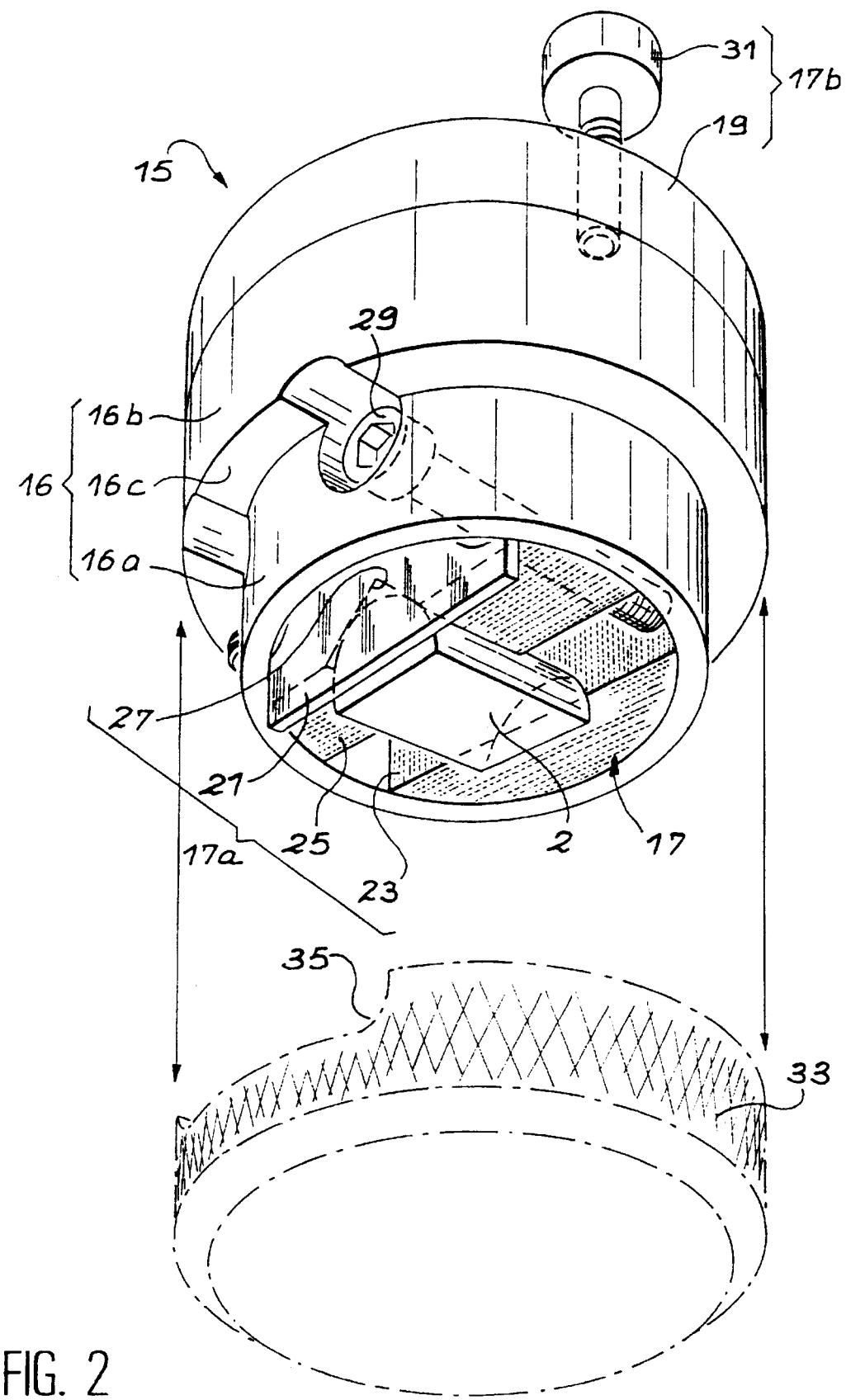
FIG. 2 diagrammatically shows the sample holder, which can be inserted in an orifice of the support disk.

FIG. 2 shows the sample holder 15. The sample holder 15 has a central body 17 with a lower portion 17a incorporating subsequently described means for positioning and holding the sample, together with an upper portion 17b incorporating a base 19 in which are inserted the means for regulating the depth reading of the sample in the disk orifice.

The sample holder also has a cylindrical jacket 16 sliding round the central body 17. The jacket 16 is externally provided with a circular shoulder 16c, which subdivides the jacket 16 into a stop ring 16b (also called upper cylinder) and a centring ring 16a (also called lower cylinder). The stop ring 16b has an external perimeter approximately equal to that of the base 19 of the central body. The centring ring 16a has a perimeter smaller than that of the stop ring 16b and which is adjusted to the perimeter of the orifice of the disk so as to be introduceable into said orifice.

The means for putting into place the material sample 2 within the sample holder 15 will now be described. It is obvious that for depositing the sample 2 in the sample holder 15, the latter must be turned round (compared with its representation in FIG. 2), the surface of the lower cylinder 17a then being directed upwards.

In FIG. 2, the sample holder 15 is shown in the position in which it is used, i.e. when it is introduced into the orifice 11 of the support disk. However, for a better understanding of the invention, a description will be given of the putting into place of the sample 2 in the sample holder 15, as if the sample holder 15 was in the reverse position of that shown in FIG. 2.

To ensure the positioning of the sample 2 in the sample holder 15, the latter has a central body 17 with a lower portion 17a located in the interior of the lower cylinder 16a. This lower portion 17a consists of a partly planar support 25. The support 25 has, essentially in its center, a V-shaped notch 27 positioned transversely to the support 25. When the sample 2 is deposited within the sample holder 15, said notch 27 permits the positioning of the sample 2 transversely with its non-planar portion (i.e. which is not to be polished) in the notch, the planar surface to be polished of said sample 2 then being oriented towards the outside of the sample holder 15.

This sample holder 15 also comprises a fixed jaw 21 and a mobile jaw 23, which together form a vice for securing the sample 2. Thus, when the sample 2 has been positioned in the notch 27, the mobile jaw 23 can be tightened by means of at least one tightening screw 29. Due to the perspective view of the sample holder in FIG. 2, only one tightening screw 29 has been shown. Advantageously, there are two parallel tightening screws 29. These tightening screws 29 pass through the lower cylinder 17a, the fixed jaw 21 and the support 25, each being screwed into a screw thread made in the mobile jaw 23. Thus, by screwing down or unscrewing said tightening screws 29, it is possible to move the mobile jaw 23 towards or away from the fixed jaw 21 and therefore tighten or loosen the vice round the sample 2.

In addition, the sample holder 15 has at its upper end a base 19, whose circumference is substantially identical to that of the stop ring 16b. This base 19, which forms the upper portion 17b of the central body 17, is joined to the stop ring 16b and supports at least three regulating or adjusting screws 31. With the sample holder shown in perspective in FIG. 2, only one of the screws 31 is visible in FIG. 2. As can be seen in FIG. 2, the screw 31 passes through the base 19 and bears against the stop ring 16b. When the sample holder 15 has been deposited in the orifice 11, said adjusting screws 31 make it possible to adjust the depth reading of the complete sample holder 15 in the orifice 11 of the disk by acting on the space between the base 19 and the stop ring 16b.

The shoulder 16c makes it possible to center the positioning of the cylinder 16a within the disk orifice, whilst the screws 31 make it possible to adjust the height at which must be located the base of the lower cylinder 16a, i.e. the planar face of the sample 2, with respect to the polishing table.

According to a preferred embodiment of the invention, it is possible to use a cover 33, shown in mixed line form in FIG. 2, in order to carry out a presetting of the planeity of the sample 2. This cover 33 is used when the sample holder is in the direction opposite to that shown in FIG. 2, just after the positioning of said sample 2 in the sample holder 15. More specifically, when the sample 2 has been positioned transversely in the notch 27 of the support 25 and before said sample 2 has been tightened between the jaws 21 and 23, it is possible to position the cover 33 above the lower cylinder 16a. The dimensions of the cover 33 are adapted to the contour of the lower cylinder 16a, so as to conform to the shape of the contour of said cylinder. The cover 33 also has a notch 35 permitting the passage of tightening screws 29. The application of said cover 33 to the lower cylinder 16a makes it possible, if the sample 2 has not been positioned in such a way that its planar surface is completely parallel to the support 25, to orient said planar surface in such a way that it is completely parallel to the support 25 and therefore perpendicular to the axis of the sample holder 15. When the planeity of the planar face of the sample 2 is ensured, it is possible to tighten the jaw 23 towards the jaw 21 so as to maintain the sample 2 in the chosen position and then remove the cover 33. The sample holder 15 can then be turned round without any risk of the sample 2 dropping and can then be introduced into an orifice of the support disk of the polishing device.

In the above description, the sample was a longitudinally cut, cylindrical sample. However, this sample holder makes it possible to examine sample shapes other than that of the sample shown in FIG. 2. For example, it is possible to examine the base of a cylindrical sample. In this case, one of the jaws or even both jaws can have an axially oriented V-shaped notch so as to better maintain the sample between the two jaws.

Thus, the sample holder according to the invention makes it possible to hold samples of random dimensions, made from all types of materials, without involving high equipment costs, because it can be introduced into all known polisher types.

It is clear that the device makes it possible to analyze material samples without requiring any resin encapsulation. Thus, the use of such a device makes it possible to reduce the quantity of waste, particularly when the waste is of a radioactive nature, because only the samples have to be recovered for storage purposes.

In addition, analysis by chemical or thermal etching can be performed on the sample directly after its polishing and without requiring any resin stripping operation. Apart from the process performance time economies, the invention permits, compared with the presently used process, economies on metallographic consumables, such as the resin, cutting wheels, abrasive paper, etc.

I claim:

1. Device for polishing samples (2) of materials, each having a substantially planar face, incorporating a polishing table (3) and a polishing head (5) equipped with a support disk (9) provided with at least one orifice (11), characterized in that it also has a sample holder (15), which can at least partly be housed in the orifice (11) of the disk and maintains the sample in a chosen position, said sample holder comprising:

a central body (17) having a lower portion (17a) with means (21, 23, 25, 27, 29) for holding and positioning the sample, and an upper portion (17b) having a base (19) in which are inserted means (31) for regulating the depth reading of the sample in the disk orifice, a sliding jacket (16) placed around the central body (17) and externally provided with a shoulder (16c), which subdivides said jacket into a stop ring (16b) having an external perimeter approximately equal to that of the base of the central body, and a smaller perimeter centring ring (16a) adjusted to the perimeter of the disk orifice.

2. Polishing device according to claim 1, characterized in that the means for holding and positioning the sample comprise a planar support (25) on which is placed the sample, a fixed jaw (21) integral with the central body and a mobile jaw (23) arranged parallel to the fixed jaw and which together form a vice able to maintain the sample in the chosen position and at least one tightening screw (29) for moving the mobile jaw with respect to the fixed jaw.

3. Polishing device according to claim 1, characterized in that the means for regulating the depth reading of the sample have at least three screws arranged regularly to one another and bearing on the stop ring.

4. Polishing device according to claim 2, characterized in that the support has a V-shaped transverse notch (27) in which the sample is positioned, its planar face being directed counter to the notch.

5. Polishing device according to claim 2, characterized in that at least one of the jaws of the holding and positioning means has a V-shaped axial notch in which the sample is locked, the planar face of the sample being directed in a direction perpendicular to that of the notch.

6. Polishing device according to claim 3, characterized in that the sample holder has a cover (33) which can be fitted around the lower portion of the central body in order to ensure a positioning of the planar face of the sample parallel to the support.

* * * * *